(12) United States Patent
Haberstroh et al.

(10) Patent No.: US 8,704,158 B2
(45) Date of Patent: Apr. 22, 2014

(54) FLUORESCENCE STANDARD, AND THE USE THEREOF

(75) Inventors: Klaus Haberstroh, Bodman-Ludwigshafen (DE); Konrad Faulstich, Stockach (DE)

(73) Assignee: Qiagen Lake Constance GmbH, Stockach (DE)

( * ) Notice: Subject to any disclaimer, the term of this patent is extended or adjusted under 35 U.S.C. 154(b) by 286 days.

(21) Appl. No.: 12/937,009

(22) PCT Filed: Apr. 17, 2009

(86) PCT No.: PCT/EP2009/002830
§ 371 (c)(1),
(2), (4) Date: Nov. 30, 2010

(87) PCT Pub. No.: WO2009/127424
PCT Pub. Date: Oct. 22, 2009

(65) Prior Publication Data
US 2011/0076687 A1 Mar. 31, 2011

(30) Foreign Application Priority Data
Apr. 17, 2008 (EP) .................................. 08007513

(51) Int. Cl.
*G01D 18/00* (2006.01)
*G01J 1/58* (2006.01)
*G01N 21/00* (2006.01)
*C12M 1/34* (2006.01)

(52) U.S. Cl.
USPC ..... 250/252.1; 250/459.1; 422/82; 435/288.3

(58) Field of Classification Search
USPC .............. 250/252.1, 459.1, 461.1; 422/82.08, 422/553, 502; 435/288.3
See application file for complete search history.

(56) References Cited

U.S. PATENT DOCUMENTS

| 2,346,661 | A | 4/1944 | Cannon, Jr. et al. |
| 3,835,782 | A | 9/1974 | Griffith et al. |
| 4,918,004 | A | 4/1990 | Schwartz |
| 5,689,110 | A | 11/1997 | Dietz et al. |

(Continued)

FOREIGN PATENT DOCUMENTS

| EP | 1703271 | 9/2006 |
| EP | 1785899 A2 | 5/2007 |

(Continued)

OTHER PUBLICATIONS

International Search Report of PCT/EP2009/002830 dated Nov. 17, 2009 (10 pages).

(Continued)

*Primary Examiner* — David Porta
*Assistant Examiner* — Faye Boosalis
(74) *Attorney, Agent, or Firm* — Miles & Stockbridge, PC

(57) ABSTRACT

The invention concerns fluorescence standards, and in particular fluorescence standards for calibrating optical detectors. According to the invention, a fluorescent mineral or mixtures of minerals are employed for use as a fluorescence standard. The fluorescent mineral can be a naturally occurring mineral or a synthetically produced mineral. Preferred fluorescent minerals for use as fluorescence standards are corundum, fluorite, turquoise, amber, zircon, zoisite, iolite or cordierite, spinel, topaz, calcium fluoride, sphalerite or zincblende, calcite or calcspar, apatite, scheelite or calcium tungstate, willemite, feldspars, sodalite, a uranium mineral, a mineral containing $Al^{3+}$, and in particular ruby and sapphire.

24 Claims, 14 Drawing Sheets

(56) References Cited

U.S. PATENT DOCUMENTS

| | | |
|---|---|---|
| 6,348,965 B1 | 2/2002 | Palladino et al. |
| 6,743,633 B1 | 6/2004 | Hunter |
| 7,384,742 B2 | 6/2008 | Montagu |
| 2002/0098588 A1 | 7/2002 | Sammak et al. |
| 2002/0151040 A1 | 10/2002 | O'Keefe |
| 2003/0012702 A1 | 1/2003 | Hudson |
| 2003/0063772 A1 | 4/2003 | Smith et al. |
| 2005/0287040 A1 | 12/2005 | Giebeler et al. |
| 2006/0134606 A1 | 6/2006 | Montagu |
| 2007/0189359 A1 | 8/2007 | Chen et al. |

FOREIGN PATENT DOCUMENTS

| | | | |
|---|---|---|---|
| JP | 10-507828 A | 7/1998 | |
| JP | 2002-500373 A | 1/2002 | |
| SU | 1718058 A1 | 3/1992 | |
| WO | WO 9006503 A2 * | 6/1990 | ............ G01N 21/64 |
| WO | 9607888 A1 | 3/1996 | |
| WO | 9934920 A1 | 7/1999 | |

OTHER PUBLICATIONS

Bernadette A. Hernandez-Sanchez et al.: "Synthesizing Biofunctionalized Nanoparticles to Iamge Cell Signaling Pathways," IEEE Transactions on Nanobioscience, IEEE Service Center, Piscataway, NY, US, Bd. 5, Nr. 4, Dec. 4, 2006, Seiten 222-230, XP011151015.4.

Felix Meiser et al., "Biofunctionalization of Fluorescent rare-Earth-Doped lanthanum Phosphate Colloidal Nanoparticles," Angewandte Chemie International Edition, Bd. 43, Nr. 44, Nov. 12, 2004, Seiten 5954-5957m XP055077079.

Timothy J. Boyle et al., "Synthesis and optical properties of naturally occurring fluorescent mineral, ferroan sphalerite, inspired (Fe,Zn)S nanoparticles," Journal of Materials Science, Kluwer Academic Publishers, Bo., Bd. 42, Nr. 8, Jan. 13, 2007, Seiten 2792-2795, XP019503181.

\* cited by examiner

FLUORESCENCE STANDARD, AND THE USE THEREOF

CROSS REFERENCE TO RELATED APPLICATIONS

This application is a §371 National Stage Application of PCT/EP2009/002830 filed Apr. 17, 2009, which claims priority to European Application 08007513.8 filed Apr. 17, 2008.

FIELD OF THE INVENTION

The invention relates to fluorescence standards or optical standards and their use, and in particular to fluorescence standards for calibrating optical detectors and fluorescence spectroscopy instruments such as microscopes, imaging devices, spectrophotometer plate readers, lateral flow detectors, and the like.

BACKGROUND OF THE INVENTION

Fluorescence refers to the short-duration, spontaneous emission of light of one wavelength upon transition of an excited electron state to a lower-energy state following excitation with light, or electromagnetic radiation in general, of a different wavelength. There are numerous natural and synthetic substances or compounds in which the phenomenon of fluorescence occurs, and which are therefore referred to as fluorophores.

In fluorescence spectroscopy, there is a need for fluorescence standards in order to have reference points for the measurements to be undertaken. Conventional fluorescence standards or fluorescent dyes generally are composed of organic compounds. The basis for these fluorescent dyes is that the molecules of the fluorescent dye emit a portion of the absorbed energy as fluorescent light at a known, different wavelength when they are irradiated with visible or ultraviolet light. These dye molecules are used in a variety of different biological assays, for example, where the fluorescence signals they emit can provide information about the system under study.

However, the prior art fluorescence standards and fluorescent dyes have one or more of the following disadvantages: They are not stable over the applicable time period, fade easily (especially under extended illumination and when illuminated with high intensities), are usable only within a narrow spectral range, are costly, are mechanically, thermally, and chemically unstable, and can age or dry out, which results in a change in the fluorescence intensity.

The object of the present invention is to provide a fluorescence standard that does not suffer the above disadvantages.

SUMMARY OF THE INVENTION

According to a first aspect of the invention, the above object is attained by the means that a fluorescent mineral, or a substance that contains a fluorescent mineral, is used as fluorescence standard. This can be a natural mineral or a synthetic mineral.

It is advantageous for the fluorescent mineral to be corundum, in particular ruby or sapphire, fluorite, chlorophane, turquoise, zircon, zoisite, iolite or cordierite, spinel, topaz, calcium fluorite, sphalerite or zincblende, wurtzite, calcite or calcspar, apatite, scheelite or calcium tungstate, powellite, willemite, feldspar, sodalite, a uranium mineral, apatite or fluorapatite or chlorapatite or hydroxylapatite, halite, tanzanite, aquamarine, tourmaline, tremolite, genthelvite, gonnardite, helvite, meionite, leucophanite, tugtupite, villiaumite, barylite, beryllite, albite, analcime, wohlerite, bustamite, celestine, chondrodite, chrysolite or clinochrysolite, chrysoberyl, hemimorphite, hexahydrite, strontianite, ammolite, andesine, ankerite, aragonite, burmite, chalcedony, cerussite, charoite, diamond, diopside, diaspore, ekanite, eudialyte, friedelite, greenockite, grossular, kunzite, lapis lazuli, lepidolite, minium, norbergite, oligoclase, opal, painite, phosgenite, phosphophyllite, rhodicite, rhodochrosite, magnesite, sulfur, shortite, siderite, spurrite, spodumene, stolzite, vanadinite, wolframite, wulfenite, YAG, zincite, cinnabar, zunyite, smithsonite, anglesite, microcline, orthoclase, danburite, laurionite, paralaurionite, vlasovite, thorite, benitoite, phenakite, eucryptite, dolomite, svabite, pectolite, tirodite, manganaxinite, esperite, roeblingite, harstigite, otavite, johnbaumite, kyanite, uvarovite, sanidine, scapolite, moissanite (SiC), cubic zirconia, amber, corals, pearls, mother of pearl, ivory, or a mineral containing $Al^{3+}$ or oxide and hydroxide minerals.

Optionally the fluorescent mineral can be doped with an activator or combinations of activators, wherein suitable activators are: divalent manganese, lead, antimony, cerium, in particular trivalent cerium, trivalent chromium, divalent or trivalent iron, trivalent or tetravalent titanium, copper, silver, divalent samarium, divalent or trivalent europium, trivalent terbium, trivalent dysprosium, trivalent holmium, trivalent erbium, uranyl compounds, ruthenium compounds, tin compounds, thallium compounds, bismuth compounds, tungstate compounds, molybdate compounds, sulfur, vanadium compounds, lanthanum compounds, praseodymium compounds, neodymium compounds, promethium compounds, gadolinium compounds, thulium compounds, ytterbium compounds, lutetium compounds.

The activators may be present in the mineral in dopings from 0.001% to 20% (percent by weight).

The fluorescent mineral can be used as a fluorescence standard in a variety of forms, for example in the form of cylinders, prisms, plates, cells, tubes, capillary tubes, cuboids, flakes, pellets or beads, nanoparticles, or as powder. In the case of beads, nanoparticles, or powder, the fluorescent mineral can be embedded or polymerized in a polymer or a carrier matrix, for example made of glass, plastic, or hydrogel. The use of a fluorescent mineral as a fluorescence standard in the form of a plurality of small particles, such as beads, improves the homogeneity of the standard, since a statistical average can be ascertained during the measurement.

Optionally, the fluorescent mineral can be functionalized for a desired application as a fluorescence standard in that functional groups with the desired function are chemically attached to the surface of the fluorescent mineral. In particular, oxide and hydroxide minerals are easy to modify chemically. Functionalized minerals can then be bound to other molecules as markers for detection as a fluorescence standard. Another type of binding can take place through encapsulation in beads, nanomaterials, polymers, gels, hydrogels, glasses, and pellets, for example, which in turn have been functionalized or can be functionalized.

Advantageously, the fluorescent mineral is used as a fluorescence standard to calibrate an optical instrument.

Advantageously, the fluorescent mineral is used as a fluorescence standard to identify a product or an object.

Advantageously, the fluorescent mineral is used as a fluorescence standard to determine the quantity of light incident on the fluorescent mineral.

Advantageously, the fluorescent mineral is used as a fluorescence standard to measure and, if applicable, to control the temperature.

According to another aspect of the invention, a sample plate for accommodating at least one sample is prepared that includes a fluorescent mineral (natural or synthetic), or a substance that includes a fluorescent mineral, as fluorescence standard.

This sample plate may be designed, for example, as a microtiter plate with a plurality of wells (e.g., 96 wells), or preferably as a well plate, wherein multiple wells extend completely through the well plate and the size of these wells is dimensioned such that a sample introduced into these wells is held in the wells against the force of gravity as a result of capillary forces.

According to the invention, the entire sample plate or only a part of the sample plate may be made of a fluorescent mineral, or a substance that includes a fluorescent mineral, as fluorescence standard.

Alternatively, in the case of a microtiter plate with a plurality of wells, the fluorescent mineral or the substance that includes a fluorescent mineral as fluorescence standard can be located in at least one of the wells, namely such that it is removable or is permanently bonded to the sample plate. In the case of the well plate with a plurality of wells, the fluorescent mineral as fluorescence standard can be located in at least one of the wells. In this alternative, the microtiter plate or the well plate itself can be made of known materials, such as plastic or glass. Preferably the fluorescent mineral as fluorescence standard has a shape (preferably cylindrical) that corresponds to the shape of the wells of the microtiter plate or the shape of the wells of the well plate.

Additional advantageous embodiments of the inventive aspects are defined in the dependent claims.

BRIEF DESCRIPTION OF THE DRAWINGS

FIG. 1b schematically shows a top view of a sample plate that is provided with the inventive fluorescent mineral as fluorescence standard from FIG. 1a.

DETAILED DESCRIPTION OF THE INVENTION

Figure 1A:
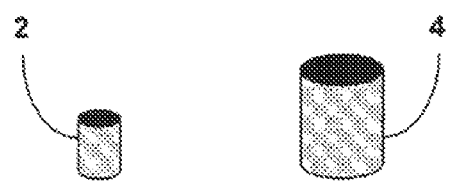
FIG. 1a shows a preferred cylindrical shape of the inventive fluorescent mineral as fluorescence standard.

As a result of extensive testing and experiments, it has been determined, surprisingly, that fluorescent minerals or substances or materials containing fluorescent minerals are suitable for advantageous use as fluorescence standards, which have numerous advantages over prior art fluorescence standards, as is evident from the following detailed description of the invention.

As is known to those skilled in the art, some naturally occurring minerals have small quantities of one or more activators, wherein the activator is present in the form of atoms, molecules, or ions that are incorporated into the crystal structure of the mineral and result in fluorescence phenomena when the mineral is excited by radiation. However, amorphous fluorescent minerals also exist. In this regard, some minerals can exhibit fluorescence over a wide wavelength range with respect to the excited and emitted light. An ideal fluorescence standard is a standard that exhibits essentially constant fluorescence intensity over the entire spectral range of the light that lies in the range of interest for the application, is economical, does not fade, and is easy to process and can be made into different shapes, is as stable over temperature as possible, is chemically inert, and does not age. In this context, chemically inert means that the fluorescence standard does not change its fluorescence properties when it is exposed to chemical substances. However, the fluorescence standard according to the invention can also be chemically functionalized as described further below.

Surprisingly, extensive experiments have demonstrated that ruby (naturally occurring or synthetic) is a fluorescence standard that approaches the ideal relatively closely. But also other materials, such as sapphire, fluorite, turquoise, amber, zircon, zoisite, iolite or cordierite, spinel, topaz, calcium fluorite, sphalerite or zincblende, calcite or calcspar, apatite, scheelite or calcium tungstate, willemite, feldspars, sodalite, a uranium mineral, or a mineral containing $Al^{3+}$ may be used. Additional fluorescent minerals that can be used according to the invention as a fluorescence standard are described in the books, "Fluorescence: Gems and Minerals under Ultraviolet Light," Manuel Robbins, GeoSciences Press, Inc., Phoenix, Ariz., 1994, and "The World of Fluorescent Minerals," Stuart Schneider, Schiffer Publishing Ltd., Atglen, Pa., 2006, which are herewith expressly referenced in full.

An individual skilled in the art will recognize that it can be advantageous in order to further improve the characteristics of the inventive fluorescence standard, especially with regard to lower wavelength dependence of the fluorescence intensity over a broad wavelength range, to provide a mixture of different fluorescent minerals which work together in such a way that the mixture has the desired wavelength dependence of the fluorescence intensity for an application.

The above minerals may be doped with one of the following activators or combinations thereof: divalent manganese, lead, antimony, cerium, in particular trivalent cerium, trivalent chromium, divalent or trivalent iron, trivalent or tetravalent titanium, copper, silver, divalent samarium, divalent or trivalent europium, trivalent terbium, trivalent dysprosium, trivalent holmium, trivalent erbium, uranyl compounds, ruthenium compounds, tungstate compounds, molybdate compounds, sulfur, and other rare earths. In this context, the activators may be present in the mineral in dopings from 0.001% to 20% (percent by weight).

An advantage of the invention consists in that the above-mentioned minerals, if applicable in combination with at least one activator, fluoresce not only under excitation with UV light, but also can be excited over a wide wavelength range, namely at wavelengths of over 600 nm in some cases.

In addition to the naturally occurring fluorescent minerals, synthetically produced fluorescent minerals (often also called synthetic gemstones) are also suitable for the inventive use as fluorescence standard. For example, the following minerals or gemstones can be produced synthetically and are commercially available: diamond, silicon carbide (moissanite), ruby, sapphire, zircon, beryl, emerald, opal, quartz, jade, topaz, turquoise, lapis lazuli, chrysoberyl, amber, spinel, tourmaline, tanzanite, zincblende, wurtzite, and others. For a detailed description of synthetic minerals or gemstones, we refer individuals skilled in the art to the following book, which is herewith expressly referenced in full: "Artificial Gemstones," Michael O'Donoughue, NAG Press, London, 2005.

Since the above-described inventive fluorescent minerals for use as fluorescence standard usually are solids, they can be provided in a variety of forms depending on the desired application as fluorescence standard, for example as flakes, cylinders, prisms, or other geometric shapes, polished or rough, cut, crushed, chipped, and preferably as powder or embedded or polymerized powder, which can be processed or prepared/produced in all sizes. Pulverization has the advantage that no waste is produced, high costs for cutting and polishing are eliminated, inhomogeneities in the fluorescence standards are averaged out, powders of different materials can be mixed together, and powders can be further embedded in other materials (e.g., polymers, resin, gels, etc.).

Preferably, the inventive fluorescent mineral for use as a fluorescence standard has a cylindrical shape, as is schematically shown in FIG. 1a. To this end, pulverized ruby (such as ruby nanoparticles), for example, can be embedded in a polymer (for example, COC [cyclic olefin copolymer], COP [cyclic olefin polymer], acrylic, and others) or a hydrogel, and molded, which is to say fully polymerized, as cylinders with different diameters and lengths. Such a cylinder can be cut into suitable, shorter cylinders as needed. This represents an easy and economical production method for different cylinder sizes. As mentioned, the inventive fluorescent mineral for use as a fluorescence standard has a cylindrical shape in FIG. 1a, with the length and diameter of the cylinder 2 being smaller than the length and diameter of the cylinder 4.

The cylindrical shape for an inventive fluorescent mineral for use as a fluorescence standard is also preferred for the reason that the inventive fluorescent mineral for use as a fluorescence standard in this form can be inserted very easily into a correspondingly shaped hole of a corresponding instrument for the purpose of calibrating the instrument, for example.

The above-described inventive fluorescent minerals for use as fluorescence standards can advantageously be integrated in a sample plate or sample carrier for accommodating a plurality of samples. This sample plate may be implemented as a microscope slide or as a microtiter plate with a plurality of wells (e.g., 96 wells), for example. In this concept, either the entire microscope slide or microtiter plate, or just a certain part thereof, can be made of an inventive fluorescent mineral for use as fluorescence standard. Alternatively, an inventive sample carrier can be designed to accommodate a plurality of capillary tubes, cells, reaction vessels, gels, polymers, tubes, and/or microfluidic chips.

In the case of a microtiter plate, the inventive fluorescent mineral for use as a fluorescence standard can be located in at least one of the wells. For example, if the inventive fluorescent mineral for use as a fluorescence standard is present in the above-described cylindrical shape, and the wells in the microtiter plate have a correspondingly complementary cylindrical shape, the inventive fluorescent mineral for use as a fluorescence standard can easily be inserted in one or more of these wells, namely such that it is removable or is permanently bonded to the sample plate, for example by adhesive bonding.

Figure 1B:
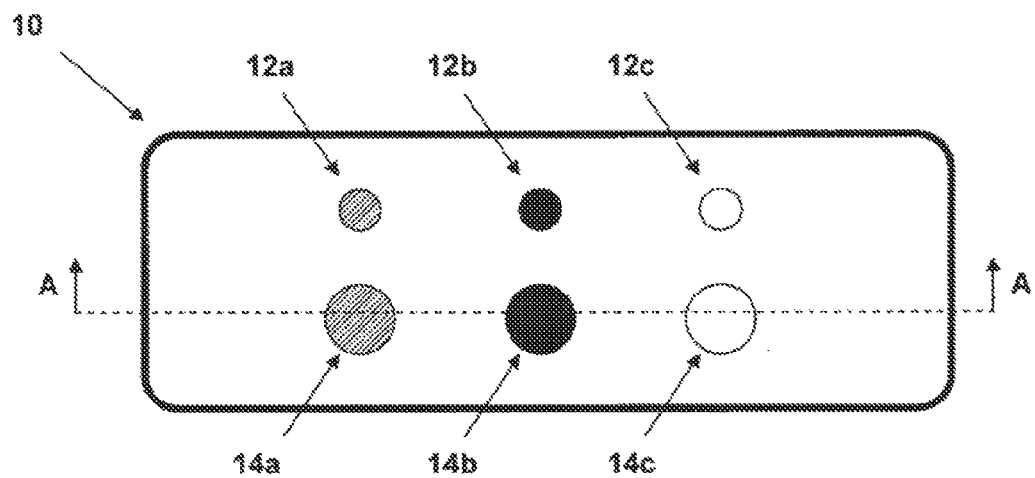
Figure 1C:
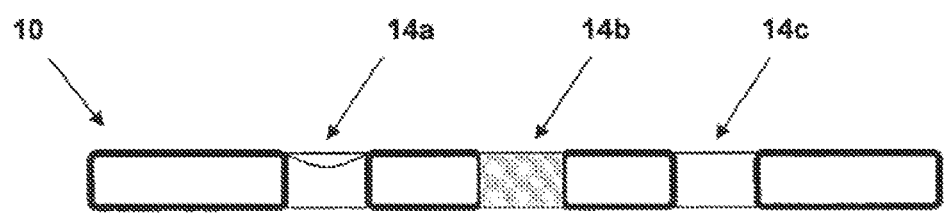
FIG. 1c shows a cross-sectional view of FIG. 1b along line A-A.

In FIGS. 1b and 1c, another preferred embodiment of a sample plate for accommodating a plurality of samples is shown, in which the above-described inventive fluorescent mineral for use as a fluorescence standard can be integrated to good advantage. The sample plate shown in FIGS. 1b and 1c is a well plate with multiple wells 12a, 12b, 12c, 14a, 14b, 14c, which extend completely through the well plate 10 and the size of these wells is dimensioned such that a sample introduced into these wells 12a, 12b, 12c, 14a, 14b, 14c is held in the wells against the force of gravity as a result of capillary forces. The well plate 10 shown in FIGS. 1b and 1c has, by way of example, 6 wells 12a, 12b, 12c, 14a, 14b, 14c, wherein groups of three wells have the same diameter, and the diameter of the wells 12a, 12b, 12c is smaller than the diameter of the wells 14a, 14b, 14c. However, an individual skilled in the art will recognize that the present invention is not restricted to the number, shape, and arrangement of wells shown in FIGS. 1a and 1b.

Just as in the case of the microscope slide and the microtiter plate, as were described above, either the entire well plate 10 or just a part thereof can be made according to the invention of a fluorescent mineral for use as a fluorescence standard.

It is preferable, however, if a fluorescent mineral for use as a fluorescence standard in the shape of a cylinder, such as the cylinders 2 and 4 from FIG. 1, is inserted in at least one of the wells of the well plate 10. Thus, for example, a fluorescent mineral for use as a fluorescence standard is located in each of the wells 12b and 14b in the well plate 10 shown in FIG. 1b. Located in the wells 12a and 14a is a liquid sample, and the wells 12c and 14c are empty. As in the case of the microtiter plate described above, a cylinder of fluorescent mineral for use as a fluorescence standard can be inserted in the well plate 10 such that it is removable, or be permanently bonded to the well plate 10, for example by adhesive bonding. Additional preferred embodiments of well plates that are suitable for the use according to the invention are described in greater detail in PCT/EP2009/002333, which is herewith expressly referenced in full.

Figure 2:
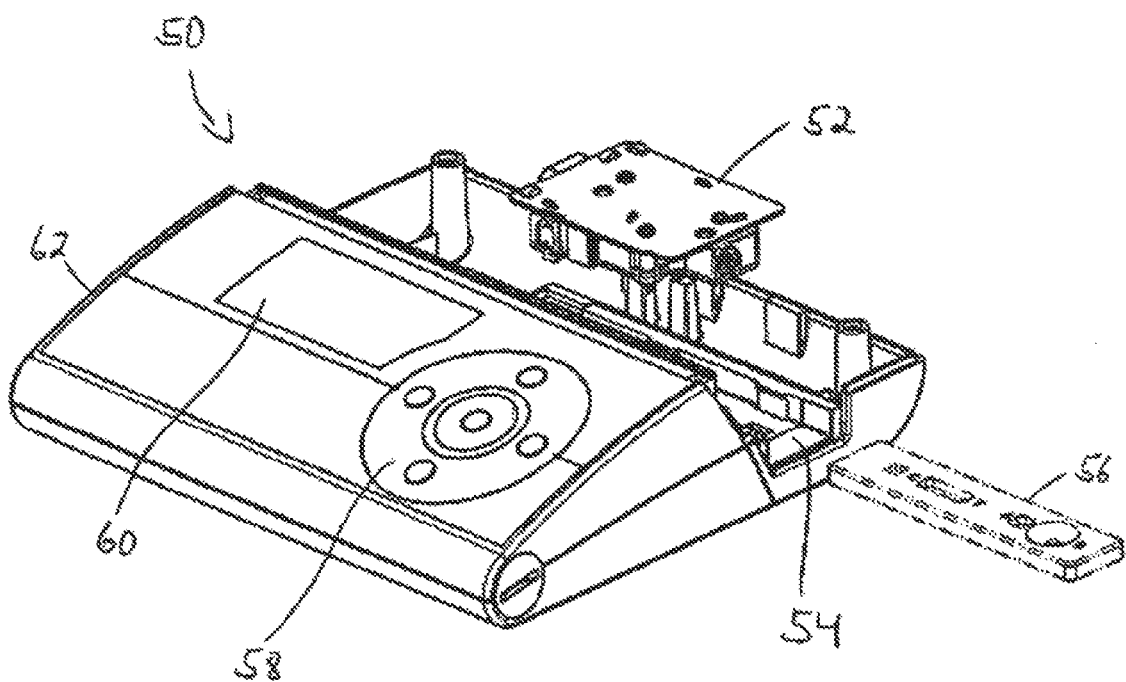
FIG. 2 schematically shows an optical reader that is especially suitable for use with the inventive fluorescence standard.

The optical measuring instrument 50 shown in FIG. 2, which is marketed by ESE GmbH of Germany and is described in greater detail in the international patent application PCT/EP2008/001468, which is herewith also expressly referenced in full, has proven to be especially suitable for the use with the above-described fluorescence standards and sample plates. The measuring instrument 50 includes a monolithic electrooptical module 52, which contains the optical and electronic components for carrying out a measurement. This module, which likewise is described in greater detail in the above-cited PCT/EP2008/001468, has a confocal design of the optics.

In addition, the measuring instrument 50 includes an insert 54 for accommodating a sample plate 56, which can be one of the above-described sample plates, namely a microscope slide, a microtiter plate, or a well plate, in which is integrated according to the invention a fluorescent mineral for use as a fluorescence standard. The sample plate 56 can be placed in the insert 54 and moved relative to the module 52. In addition or alternatively, the module 52 can be moved relative to the sample plate 56. The measuring instrument 50 is additionally equipped with a keypad or control panel 58 for controlling the measurements, and a display 60 for displaying the measurement results that have been obtained.

The above-described inventive fluorescence standards and sample plates made of such fluorescence standards are suitable for the calibration of instruments that are used for measuring steady-state fluorescence, time-resolved fluorescence, fluorescence lifetime, and/or fluorescence polarization. In this context, the concept calibrating or calibration relates to the wavelength of the fluorescence signal, the intensity of the fluorescence signal, the lifetime or length of the fluorescence signal, and/or the orientation of a sample plate. The orientation can be controlled or regulated by a movement of the plate relative to an optical reader, namely into a position in which, for example, the maximum fluorescence intensity is observed.

The inventive fluorescence standards should be used to monitor the accuracy and operational functionality of fluorescence sensors, for example. The fluorescence standards can be built into, e.g., analytical instruments (such as the above-described optical measuring instrument 50) in order to guarantee the functionality of these instruments. For example, the instruments perform a self-test that includes the sensor functions. In doing so, the sensor illuminates the fluorescence standard and measures the fluorescence intensity of the standard. This value is then compared to a stored value. If both values lie within the permitted tolerance range, then the self-test is reported as passed. During this process, the light source, and the detector, and the electronics, and also the mechanical parts (if the sensor has to be moved initially) of the instrument are checked.

The use of the inventive fluorescent minerals is not limited only to intensity measurements. Fluorescence can be carried out as an intensity measurement, but also in a time-resolved fashion as a lifetime determination of the excited state, as a polarization measurement, as a phase-shift measurement with a fluorescence excited with a modulated intensity, and as a measurement of the rotational correlation time, since the fluorescent molecules can move during the time delay from excitation to emission and, if emitting in a polarized manner, can radiate light over a specific solid angle. The inventive fluorescent minerals or mixtures thereof can therefore be used as standards for all of these types of fluorescence measurements.

The use of the inventive fluorescent minerals is not limited to their use as fluorescence standards; rather, the minerals can also be used as color standards or reflectometric standards, in general as optical standards.

Similarly, the inventive fluorescence standards can be functionalized, for example through the chemical attachment of functional groups to the surface. An individual skilled in the art will recognize that oxides such as corundum/ruby/sapphire or silicates can be equipped relatively easily and with all possible functional groups by means of silicon chemistry (silanes, siloxanes). Furthermore, it is also possible to encapsulate the inventive fluorescent minerals in pellets or beads, in particular nanobeads, and use them in a flow counter.

It is further possible according to the invention to uniquely identify any desired products or objects with the inventive fluorescence standards. The inventive fluorescent minerals for use as fluorescence standards are, namely, stable with regard to light, temperature and other influences, so that, e.g., labels, bar codes, packaging, etc. can easily be provided therewith, and can still be reliably read or recognized after a relatively long period of time. In this design, one can use various stable fluorescent minerals as fluorescence standard, and deduce the original object on the basis of the color or intensity combinations at different wavelengths. This is important, for example, at the cash register of a supermarket, when multiplexing biochemical assays, at customs, to identify supply chains and originals, for forgery-resistant identification cards, money, and, e.g., for customized and traceable artists' paints.

Furthermore, by using their fluorescence properties as a temperature detector, the inventive fluorescent minerals or substances that contain such an inventive mineral can be used to monitor temperatures and for temperature calibration of measurements. Since the strength of the fluorescence depends on the temperature of the inventive fluorescent minerals, and they have a relatively high melting point (the melting point of ruby, for example, is approximately 2050 degrees Celsius) one can ascertain temperature through fluorescence measurement based on the fluorescence intensity, if applicable at different wavelengths or even at a single wavelength. In this context, it is especially interesting that only a very few conventional temperature measurement devices cover a range of up to more than 2000 degrees Celsius, something which, however, is very important for industrial sintering processes, for instance.

Another advantage of, e.g., ruby is that it is nontoxic and is difficult to dissolve. This permits its use in medical technology, for example in implants, and for many diagnostic purposes, for example as a standard for monitoring the glucose content in implants.

EXAMPLES

1. Commercially available colored glasses were compared with the inventive minerals for use as fluorescence standard. Here, excitation (abbreviated as Ex in the figures) took place at values in a range from 365 nm to 660 nm, and emission (abbreviated as Em in the figures) was measured at values in a range from 480 nm to 720 nm with the above-described measuring instrument 50 implemented as an ESE FluoSens sensor.

The comparison glasses used are the commercially available colored glasses from the Schott glass company, with the product names OG 550 (melt number: 339636, dimensions 50.0×50.0 mm, thickness 1.0 mm), OY 530 (dimension 13.0 mm, diameter, thickness 2.0 mm), and OY 570 (dimension 13.0 mm, thickness 2.0 mm).

Figure 3A:
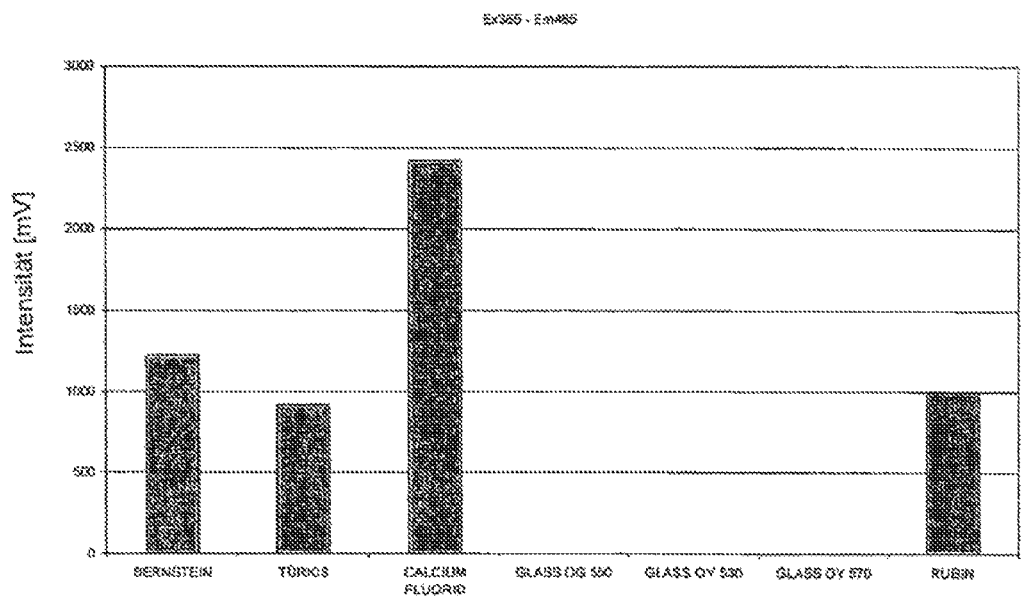
FIGS. 3a through 3n show, in the form of bar graphs, measured fluorescence intensities for inventive fluorescence standards and, for the purpose of comparison, some conventional fluorescence standards at different excitation and emission wavelengths.
Figure 3B:
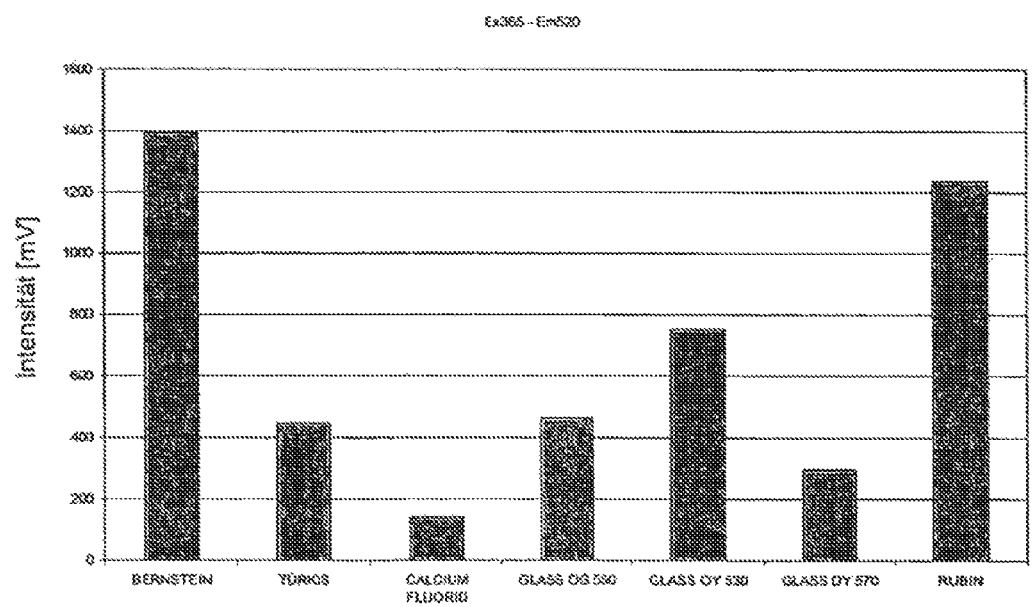
Figure 3C:
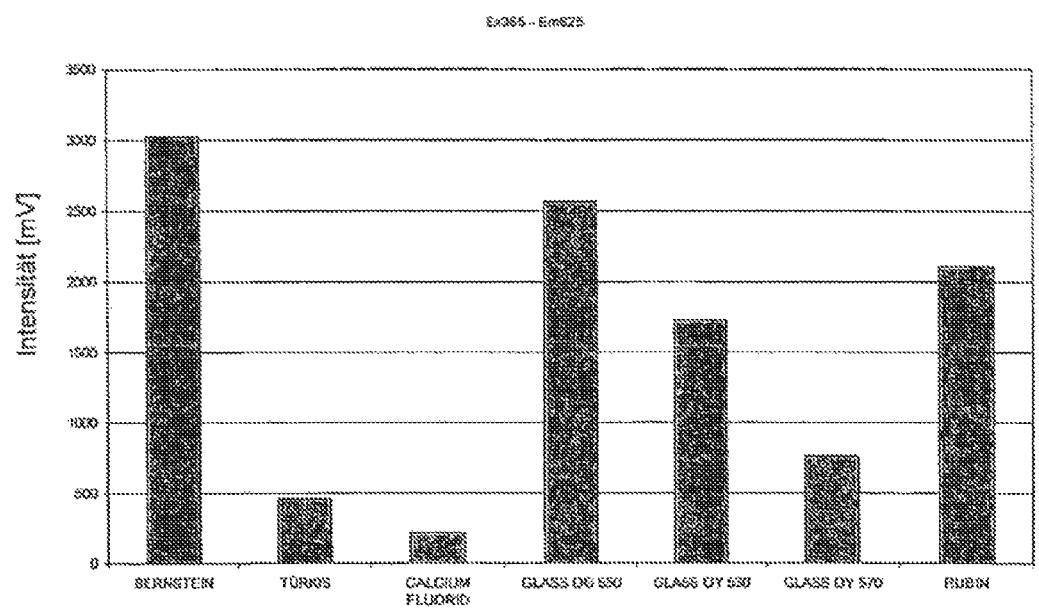
Figure 3D:
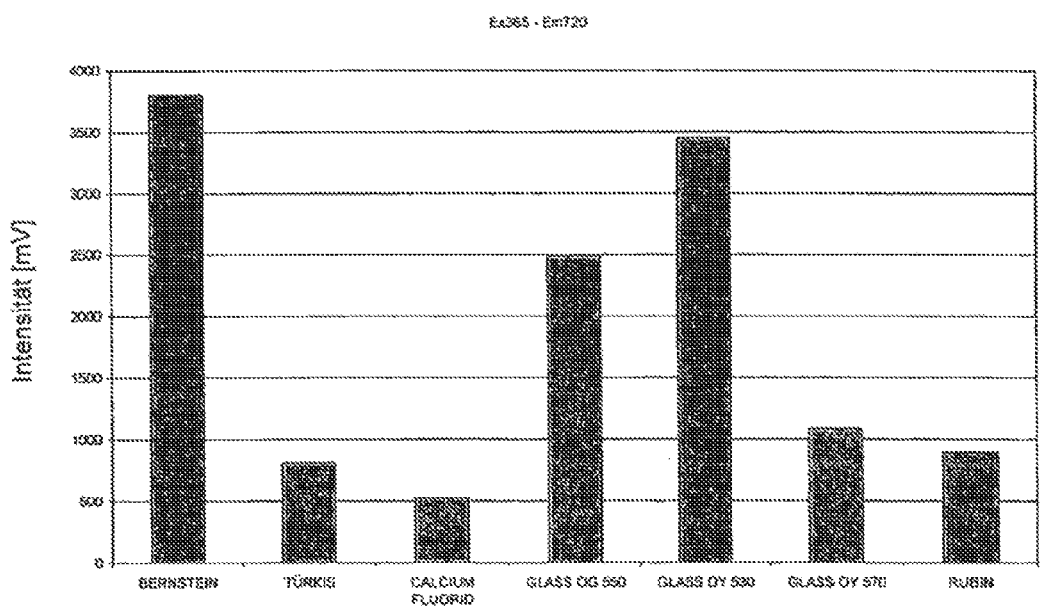
Figure 3E:
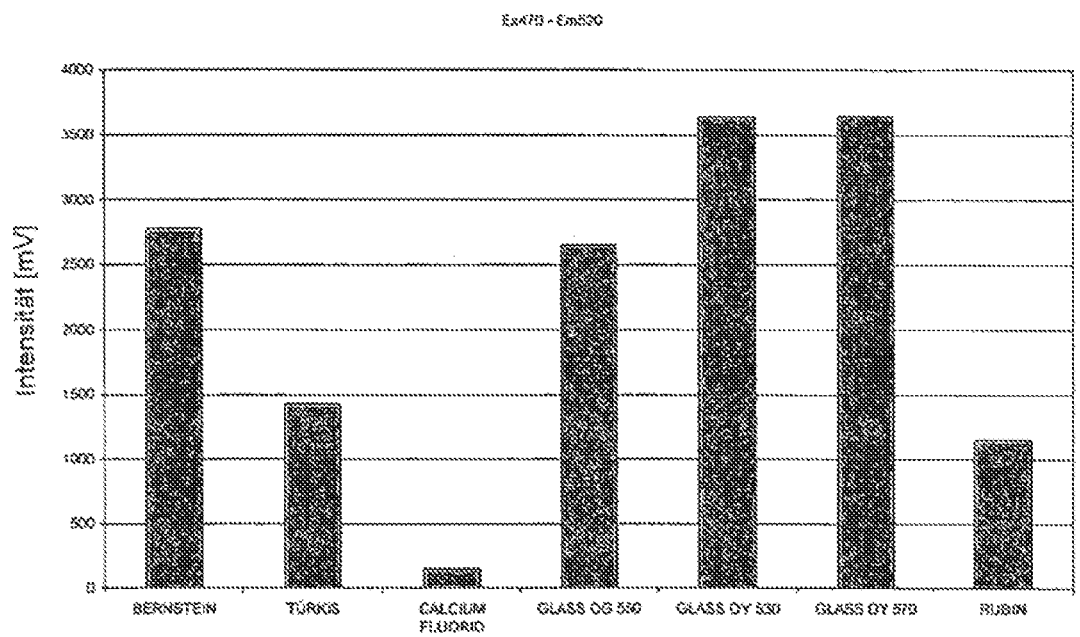
Figure 3F:
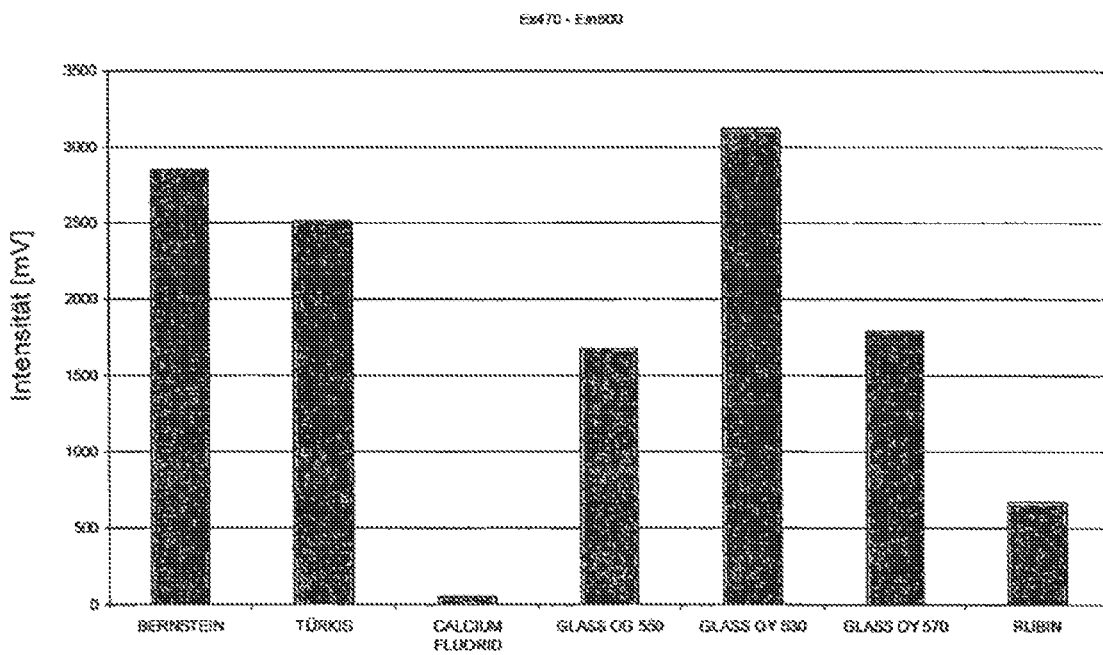
Figure 3G:
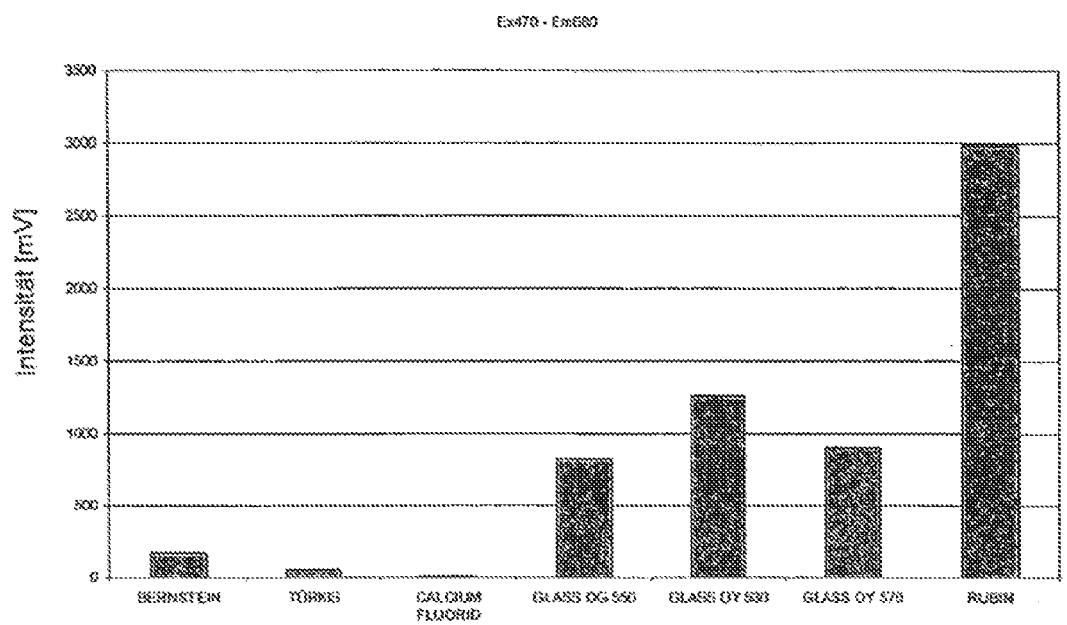
Figure 3H:
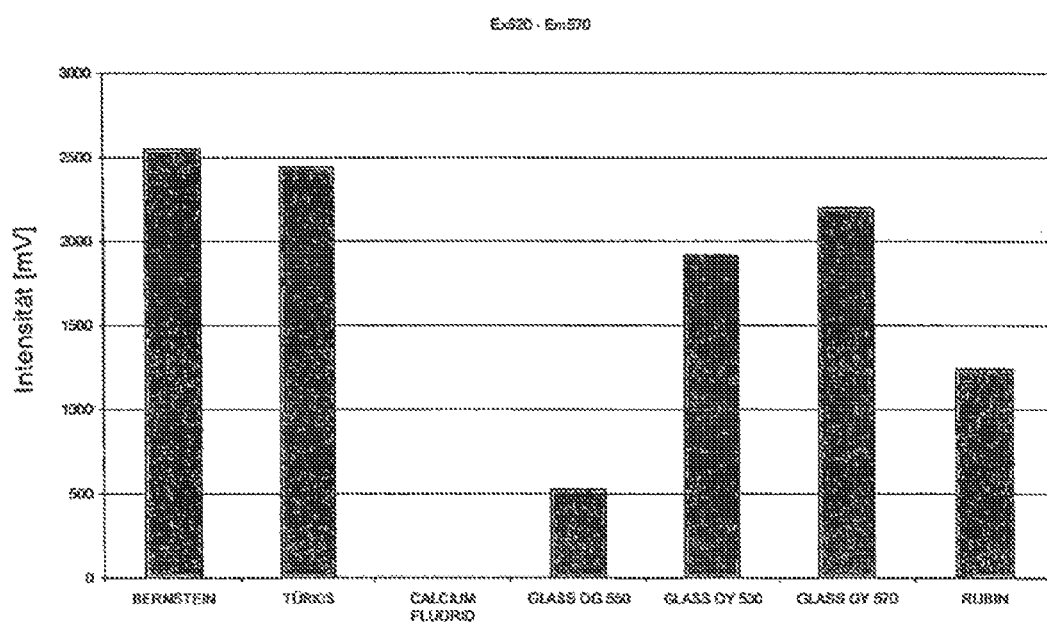
Figure 3I:
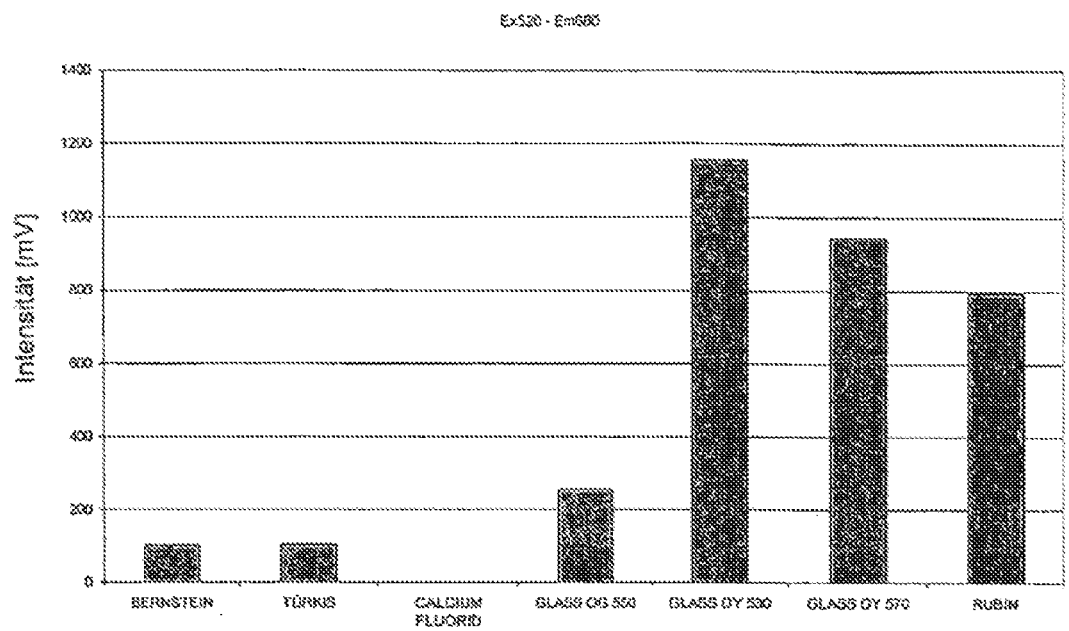
Figure 3J:
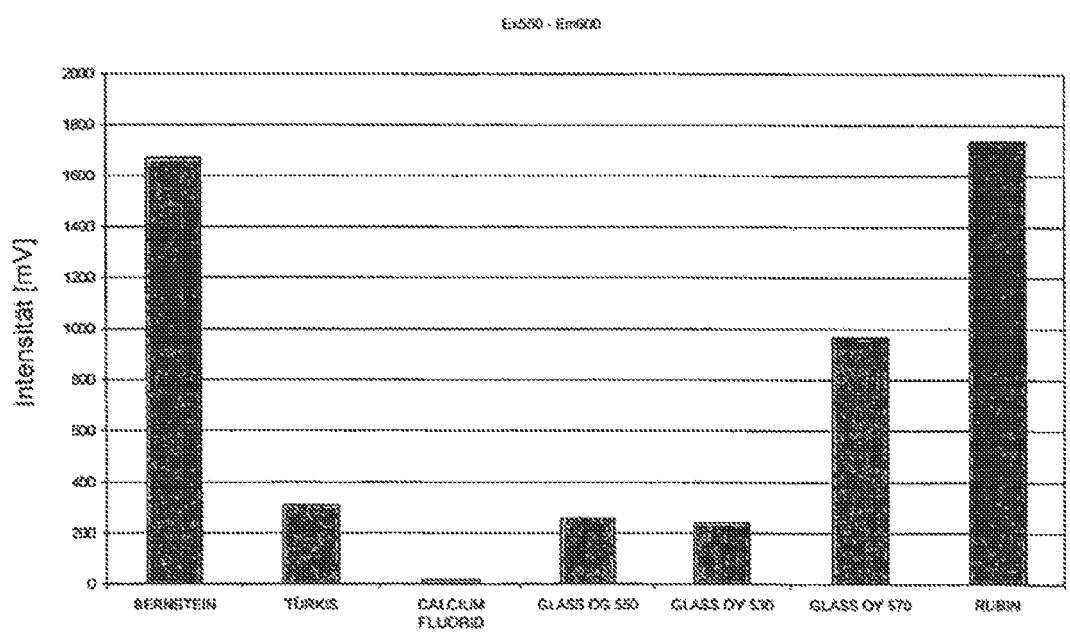
Figure 3K:
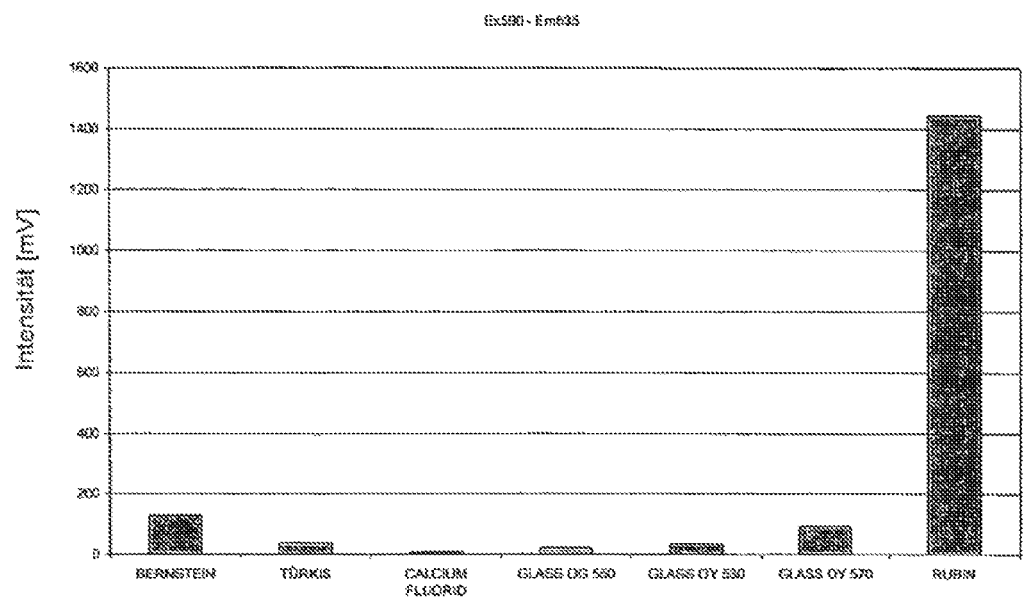
Figure 3L:
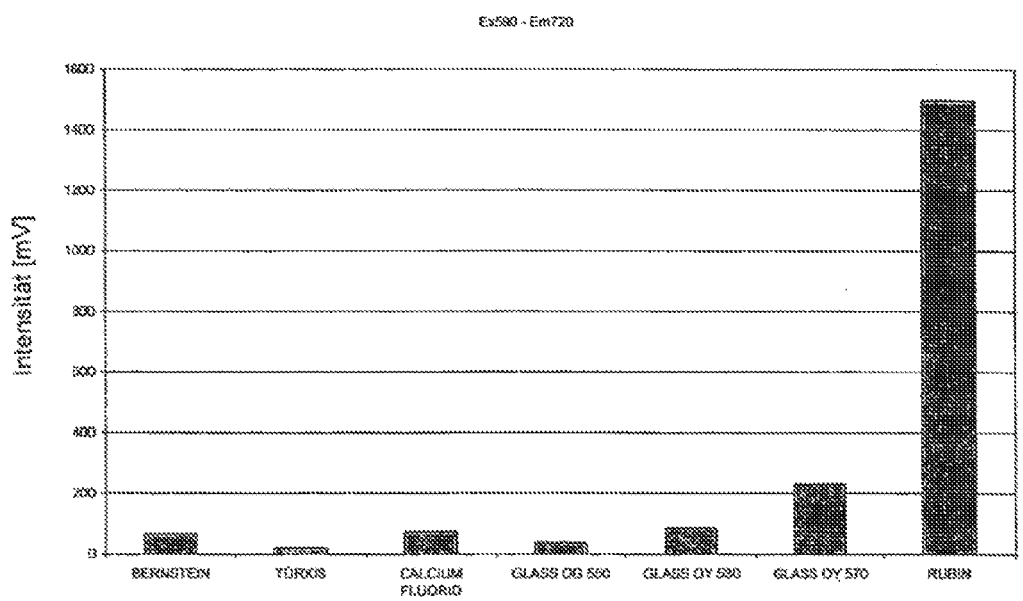
Figure 3M:
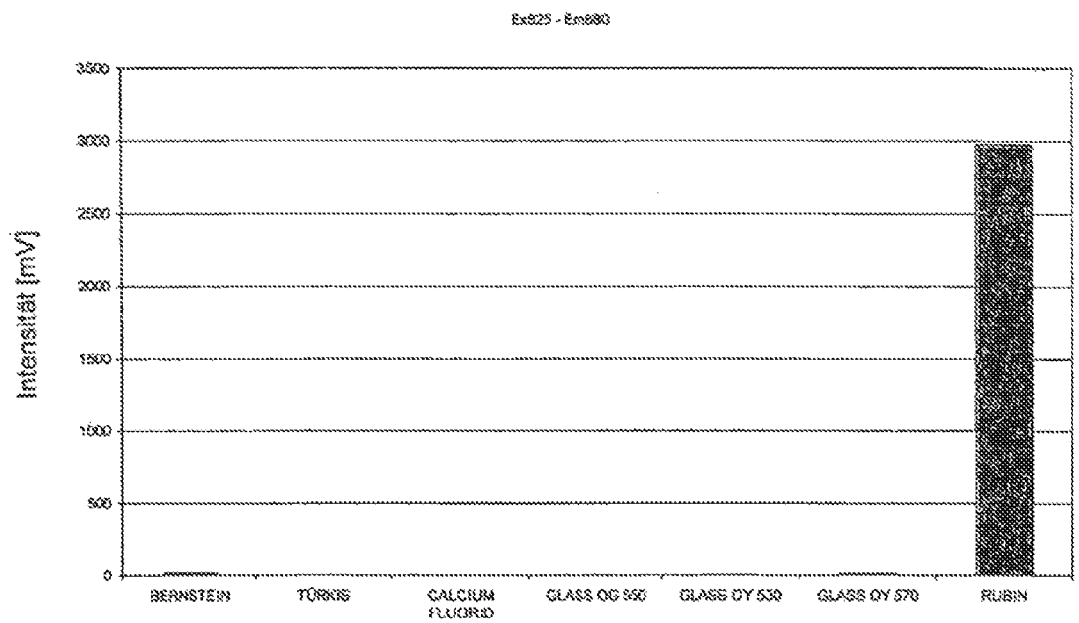
Figure 3N:
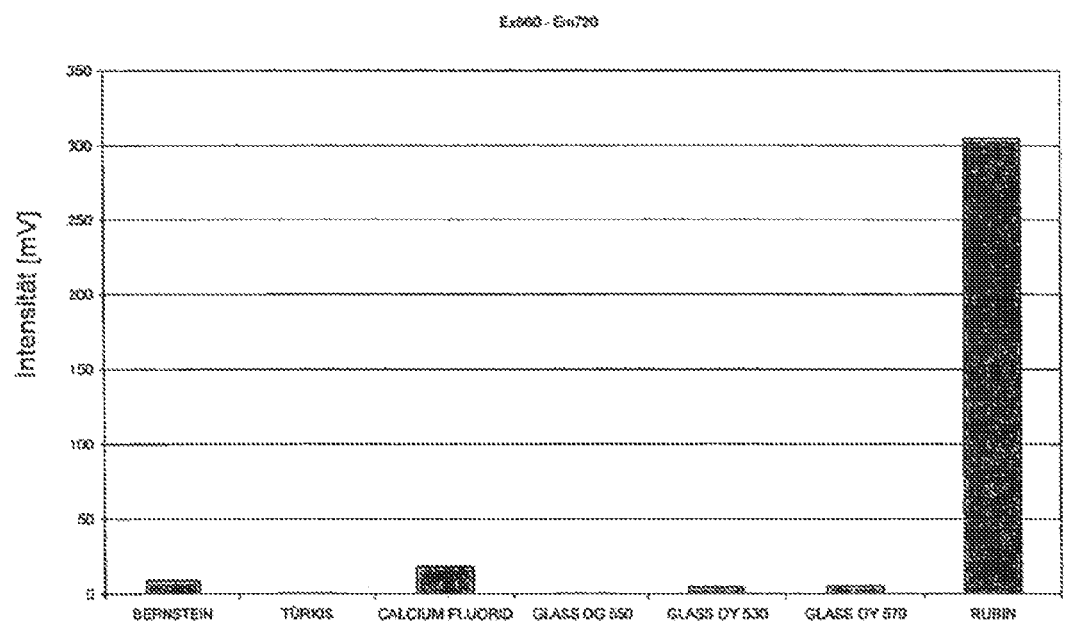
Figure 4A:
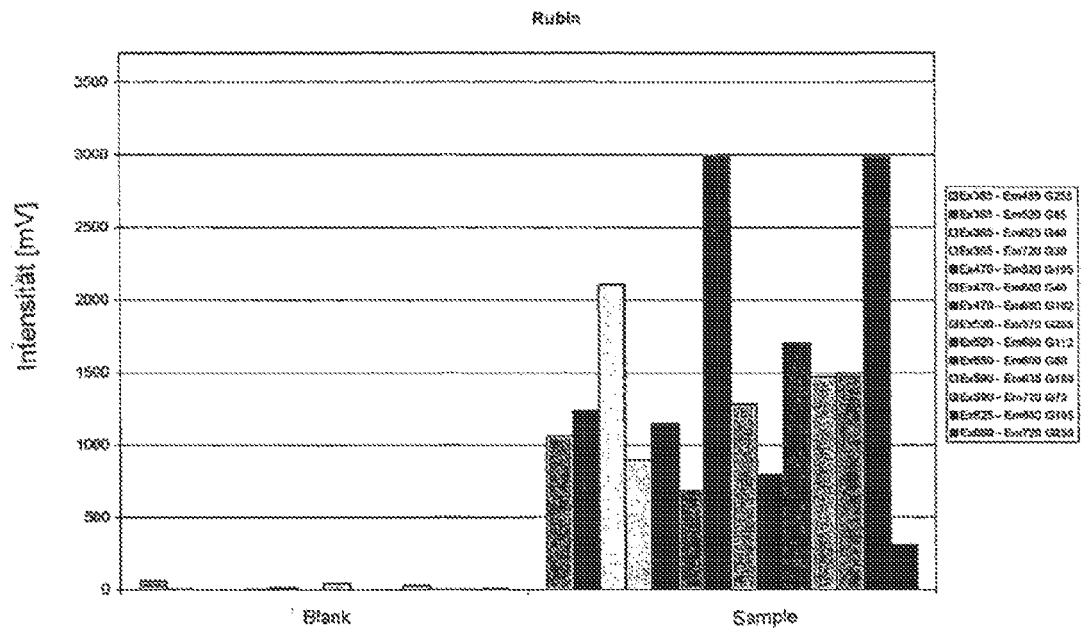
FIGS. 4a through 4f show, in the form of bar graphs, measured fluorescence intensities for inventive fluorescence standards and, for the purpose of comparison, some conventional fluorescence standards at different excitation and emission wavelengths in an overview.
Figure 4B:
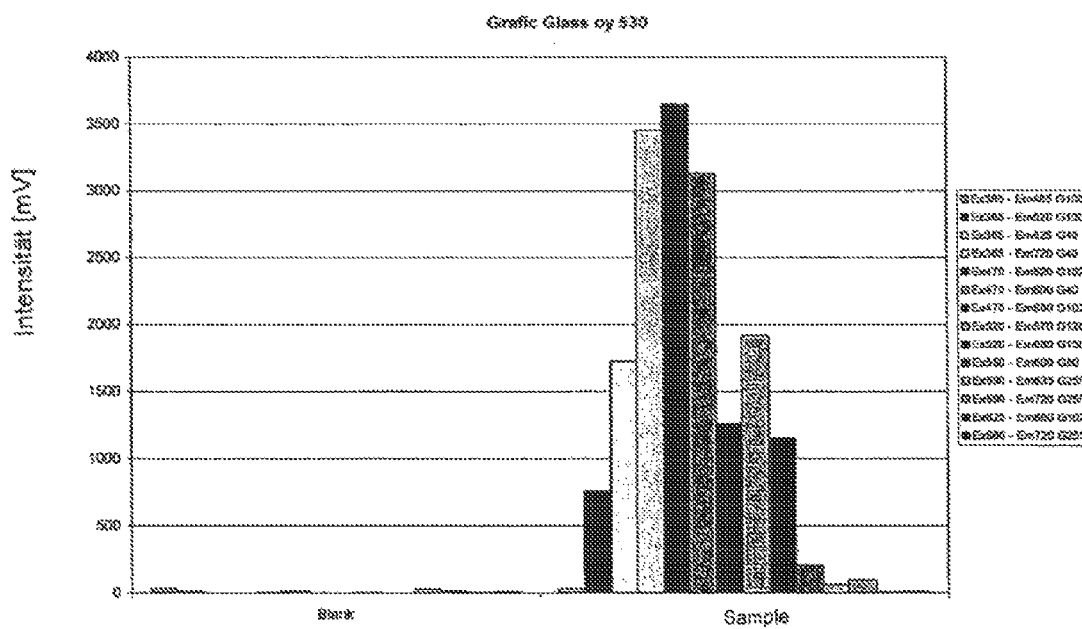
Figure 4C:
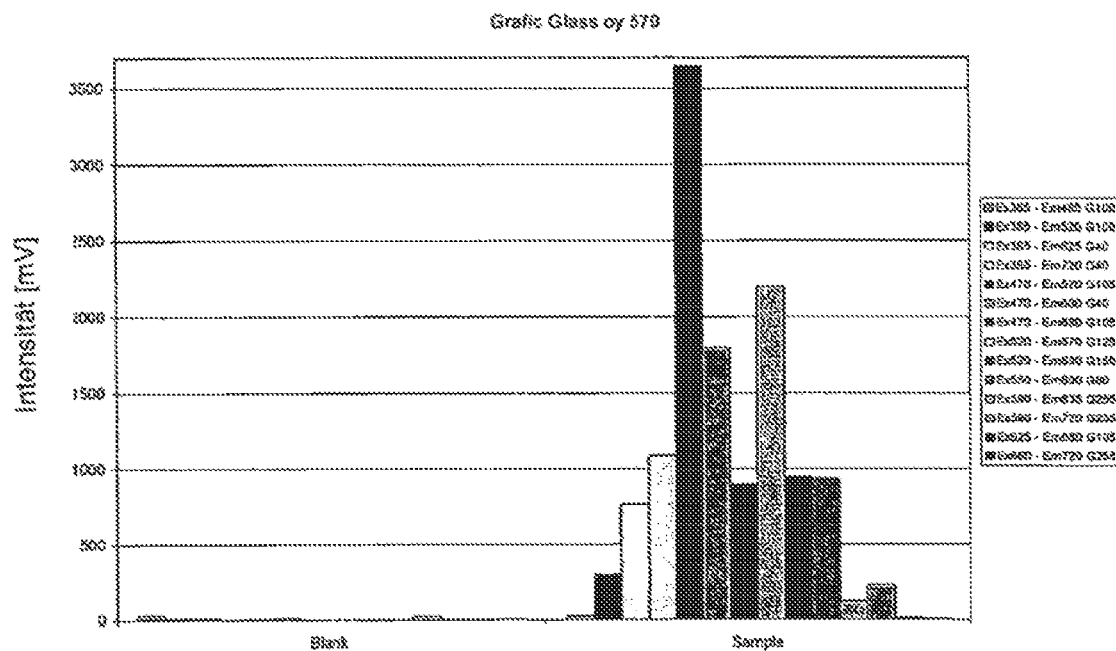
Figure 4D:
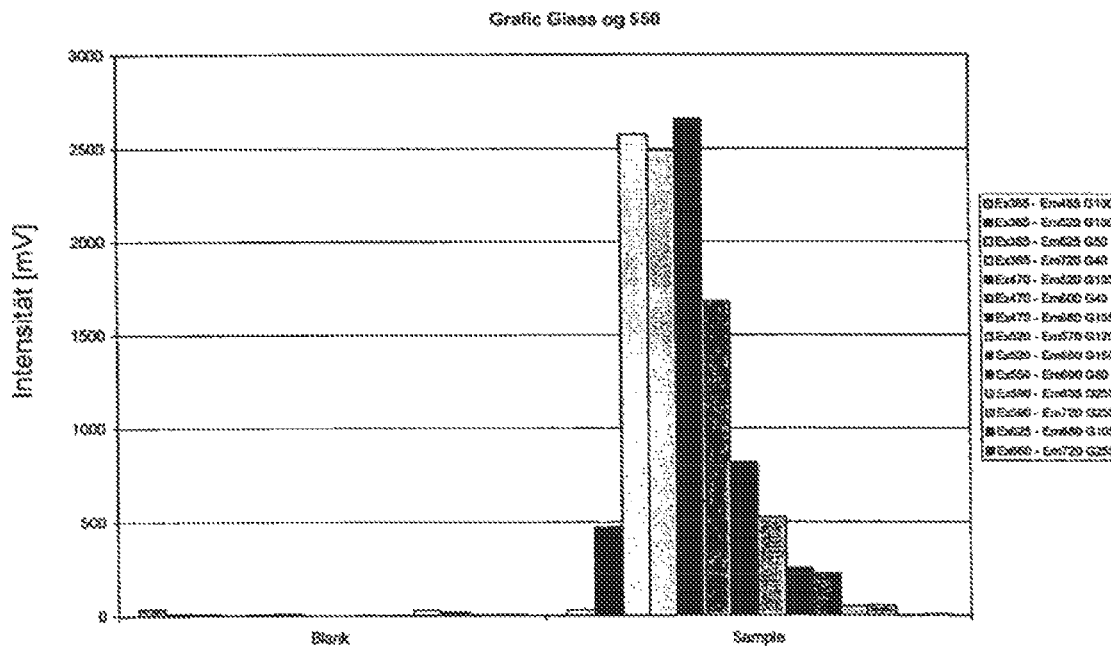
Figure 4E:
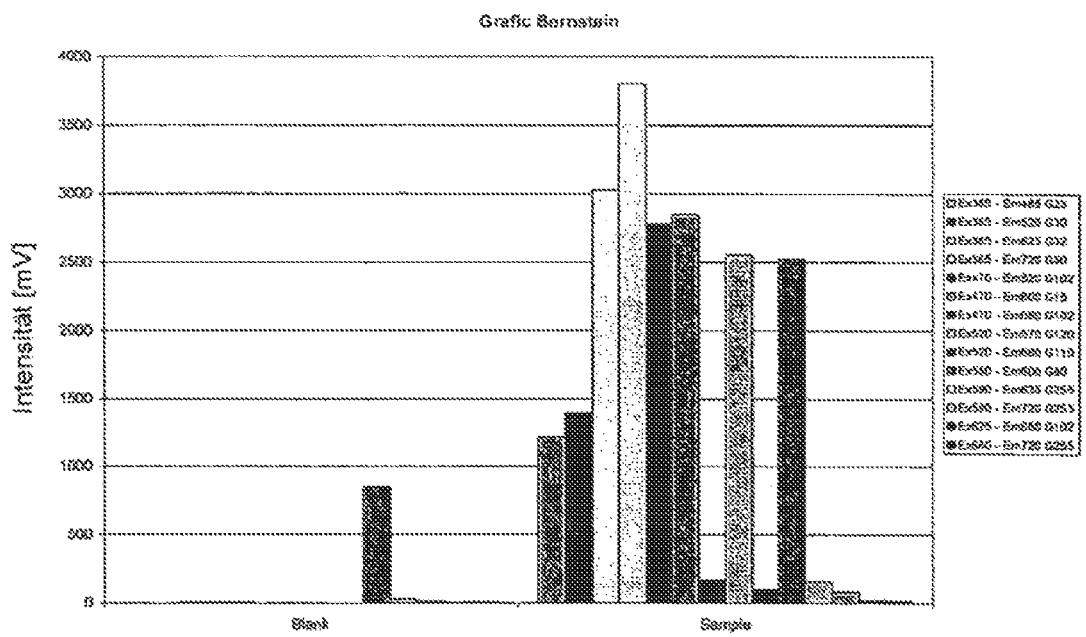
Figure 4F:
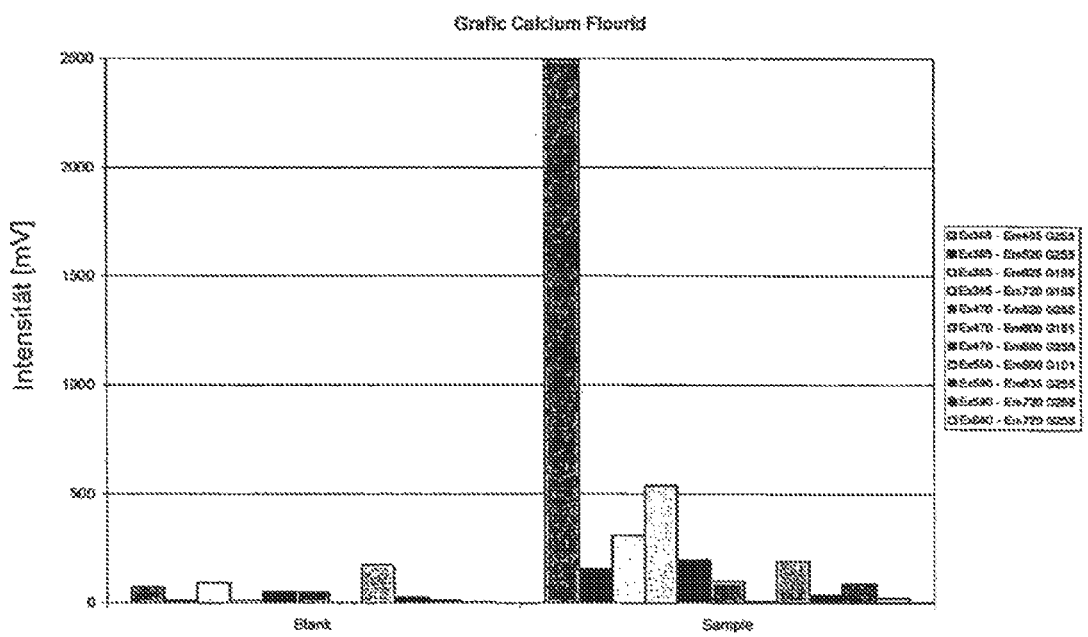

FIGS. 3a through 3n show, in the form of bar graphs, the measured fluorescence intensities in mV for ruby, amber, turquoise, calcium fluoride, and the three different fluorescence standards available from Schott, namely the glasses OG 550, OY 530, and OY 570, at different excitation and emission wavelengths.

The limited applicability of the commercially available glasses employed as fluorescence standards is immediately apparent, since they show a very slight signal, or even no signal, at many wavelength combinations (excitation (Ex)/detection (Em)).

In contrast, ruby, for example, shows a very distinct fluorescence signal at nearly all wavelength combinations, but especially also at higher wavelengths. In this range, virtually no organic compounds exist for use as fluorescence standards that are "light resistant," which is to say that do not fade (bleach) under relatively long irradiation. Another advantage of the inventive fluorescent minerals, in particular ruby, is the distinct fluorescence intensity with a large "Stokes shift," which is to say the difference between the excitation wavelength (Ex) and the emission wavelength (Em).

FIGS. 4a through 4f show the measured fluorescence intensities for the investigated materials at different wavelengths in an overview in the form of bar graphs. The parameter G listed in the figure key stands for the sensitivity setting of the fluorescence sensor. In general, the higher the numeric value for G is, the higher the sensitivity. G relates to the power of the LED for excitation. The higher the power to the LED is, the brighter it shines and the more efficient the excitation is. Again, the pronounced fluorescence intensity over a wide wavelength range is especially noticeable for ruby.

Figure 5:
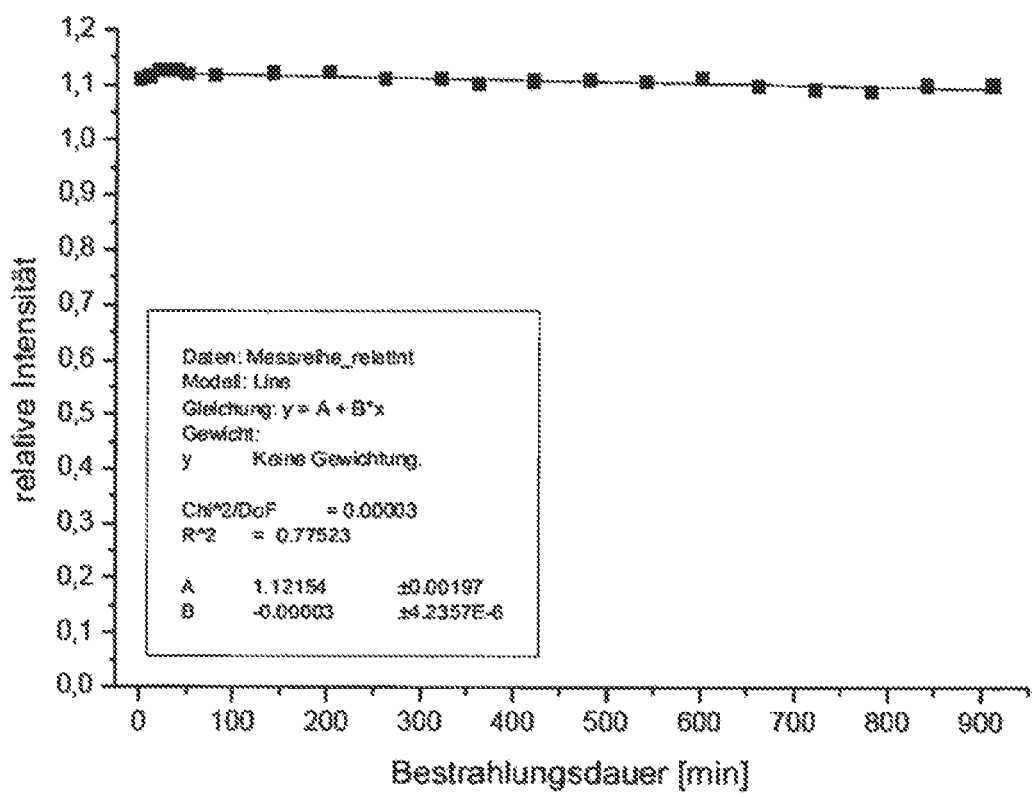
FIG. 5 shows the measured fluorescence intensity of an inventive fluorescence standard in the form of a ruby as a function of the duration of irradiation with light at an excitation wavelength of 532 nm.

3. FIG. 5 shows the results of a "bleaching" test that was performed with a laser with an output of 18 MW at an excitation wavelength of 532 nm. In this test, a ruby was irradiated or excited with the laser for time periods of different lengths, and the fluorescence intensity was measured. The graph shows a regression line that is essentially horizontal, which is to say the fluorescence intensity of the ruby is independent of the duration of irradiation and virtually does not decrease, in particular for longer irradiation durations. In other words, when an inventive ruby is used as fluorescence standard, no fading (bleaching) of the fluorescence standard occurs. We note here for the purpose of comparison only that conventional, organic fluorescence standards or dyes fade substantially at an excitation wavelength of 532 nm with the strength of sunlight in just a few minutes, which is several orders of magnitude less intensive than the excitation light used in this experiment, which was generated by a laser with an output of 18 MW.

Figure 6:
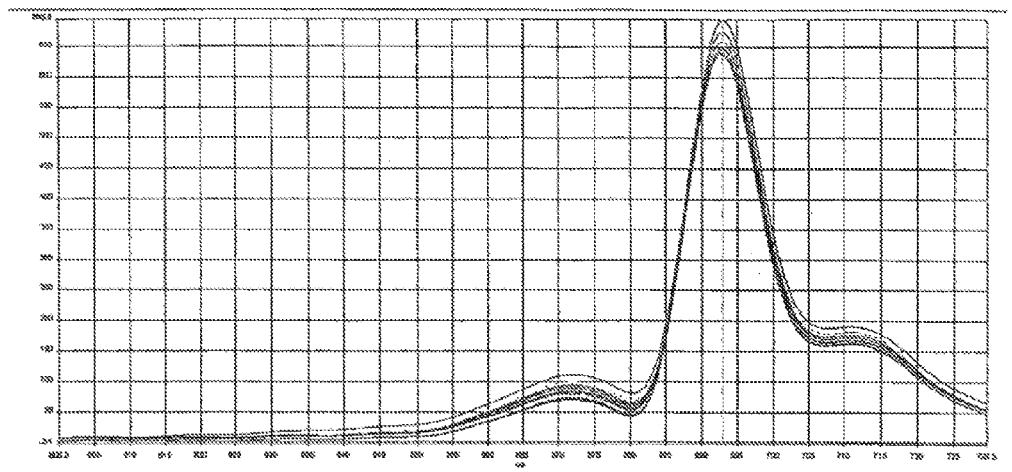
FIG. 6 shows the temperature dependence of the emission spectrum of an inventive fluorescence standard in the form of ruby.

4. FIG. 6 shows a graph of the measured fluorescence intensities as a function of the wavelength for a ruby at different temperatures. The ruby was excited with light at a wavelength of 400 nm. The different curves show the measurements at temperatures between room temperature and approximately 65 degrees Celsius, with the maximum fluorescence intensity having been measured at an emission wavelength of approximately 693 nm at a temperature of approximately 65 degrees Celsius.

Figure 7:
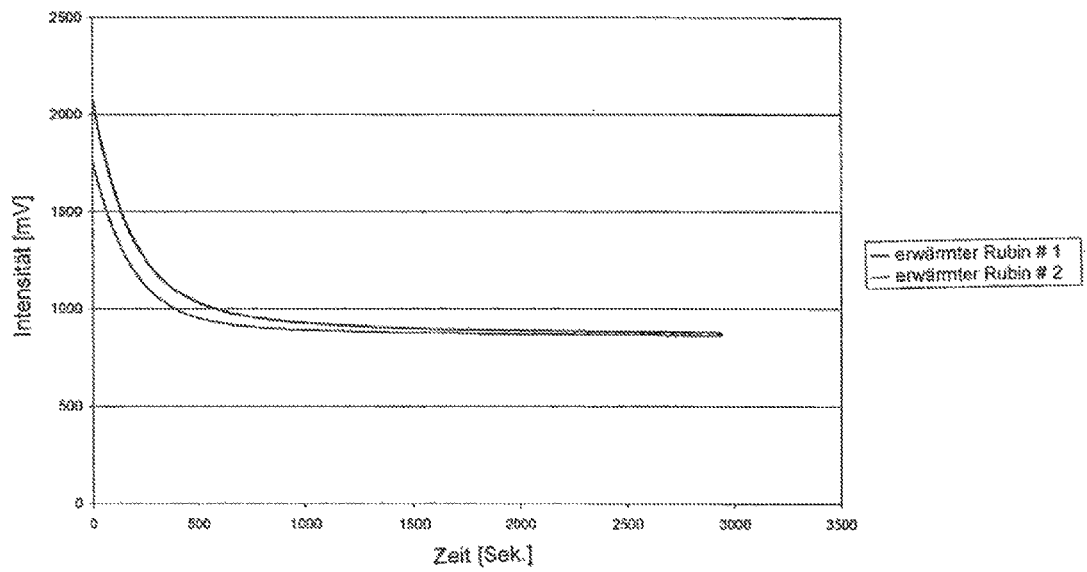
FIG. 7 shows the fluorescence intensity of an inventive fluorescence standard in the form of ruby heated to approximately 200 or 250 degrees Celsius as a function of time.

5. FIG. 7 shows the fluorescence dependence of a ruby on temperature in another form. In this experiment, a ruby was heated with a heat gun to approximately 200 or 250 degrees Celsius. After the application of heat by the heat gun was stopped at the time t=0, the ruby cooled back down to room temperature. During this cooling phase, which is to say with decreasing temperature, of the ruby, the fluorescence intensity was measured at the same wavelength (470 nm) and intensity of the excitation light as a function of time, and hence of temperature. The measurement took place at a wavelength of 520 nm.

An individual who is skilled in the art will easily recognize that the inventive fluorescent minerals, or substances that contain such fluorescent minerals, described here can be used to advantage in ways other than those described above, and these likewise are intended to be included in the scope of protection of the invention, as defined by the attached claims. In particular, an individual who is skilled in the art will recognize that the term "fluorescence standard" used here should be broadly construed and includes all applications in which the fluorescence characteristic of the inventive minerals is used, which is to say after suitable excitation to emit electromagnetic radiation with measurable physical properties (for example, such as intensity, polarization, lifetime, phase shift, rotational correlation time) at a well defined wavelength.

What is claimed is:

1. A sample plate for accommodating at least one sample, the plate being adapted to be accommodated in an optical measuring instrument that uses fluorescence measurement, and the plate being a well plate in which multiple wells extend completely through the well plate and the size of the wells is dimensioned such that a sample introduced into the wells is held in the wells against the force of gravity as a result of capillary forces, wherein a fluorescent mineral and/or a substance that includes a fluorescent mineral, for use as a fluorescence standard, is removably located in at least one of the wells of the well plate, and has a shape that corresponds substantially to the shape of wells of the well plate.

2. The sample plate of claim 1, wherein said fluorescent mineral is a naturally occurring mineral and/or a synthetically produced mineral.

3. The sample plate according to claim 1, wherein the fluorescent mineral is corundum, fluorite, chlorophane, turquoise, zircon, zoisite, iolite or cordierite, spinel, topaz, calcium fluorite, sphalerite or zincblende, wurtzite, calcite or calcspar, apatite, scheelite or calcium tungstate, powellite, willemite, feldspar, sodalite, a uranium mineral, apatite or fluorapatite or chlorapatite or hydroxylapatite, halite, tanzanne, aquamarine, tourmaline, tremolite, genthelvite, gonnaraite, helvite, meionite, leucophanite, tugtupite, villiaumite, barylite, beryllite, albite, analcime, wohlerite, bustamite, celestine, chondrodite, chrysolite or clinochrysolite, chrysoberyl, hemimorphite, hexahydrite, snontianite, ammolite, andesine, anketite, aragonite, burmite, chalcedony, cerussite, charoite, diamond, diopside, diaspore, ekanite, eudialyte, friedelite, greenockite, grossular, kunzite, lapis lazuli, lepidolite, minium, norbergite, oligoclase, opal, painite, phosgenite, phosphophyllite, rhodicite, rhodochrosite, magnesite, sulfur, shortite, siderite, spurrite, spodumene, stolzite, vanadinite, wolframite, wulfenite, YAG, zincite, cinnabar, zunyite, smithsonite, a giesite, microchne, orthoclase, danburite, laurionite, paralaurionite, viasovite, diorite, benitoite, phenakite, eucryptite, dolomite, svabite, pectolite, tirodite, manganaxinite, esperite, roeblingite, harstigite, otavite, johnbaumite, kyanite, avarovite, sanidine, scapoiite, moissanite (SiC), cubic zirconia, amber, corals, pearls, mother of pearl, ivory, and/or a mineral containing $Al^{3+}$ or oxide and hydroxide minerals.

4. The sample plate according to claim 1, wherein the fluorescent mineral contains an activator or a combination of activators, which has or have been selected from the following group: divalent manganese, lead, antimony, cerium, in particular trivalent cerium, trivalent chromium, divalent or trivalent iron, trivalent or tetravalent titanium, copper, silver, divalent samarium, divalent or trivalent europium, trivalent terbium, trivalent dysprosium, trivalent holmium, trivalent erbium, uranyl compounds, ruthenium compounds, tin compounds, thallium compounds, bismuth compounds, tungstate compounds, molybdate compounds, sulfur, vanadium compounds, lanthanum compounds, praseodymium compounds, neodymium compounds, promethium compounds, gadolinium compounds, thulium compounds, ytterbium compounds, lutetium compounds.

5. The sample plate according to claim 4, wherein the activator or activators is or are contained in the mineral in dopings from 0.001% to 20% (percent by weight).

6. The sample plate according to claim 1, wherein the fluorescent mineral or the substance that includes a fluorescent mineral is present in the form of cylinders, prisms, plates, flakes, pellets or beads, nanoparticles, or powder.

7. The sample plate according to claim 1, wherein the fluorescent mineral or the substance that includes a fluorescent mineral is embedded or polymerized in a polymer, gel, hydrogel, glass, or a carrier matrix.

8. The sample plate according to claim 1, wherein the use as fluorescence standard includes measurement of the intensity, polarization, lifetime, phase shift and/or rotational correlation time of the fluorescence.

9. The sample plate according to claim 1, wherein the fluorescent mineral or the substance that includes a fluorescent mineral is functionalized for a desired application as a fluorescence standard in that functional groups with the desired function are chemically attached to the surface of the fluorescent mineral.

10. The sample plate according to claim 1, wherein the fluorescent mineral or the substance that includes a fluorescent mineral is embedded in a nanoparticle for a desired application.

11. The sample plate according to claim 1, wherein the fluorescent mineral or the substance that includes a fluorescent mineral is used as a fluorescence standard to calibrate an optical instrument.

12. The sample plate according to claim 1, wherein the fluorescent mineral or the substance that includes a fluorescent mineral is used as a fluorescence standard in order to carry out an instrument self-test of an optical measuring instrument or to check the functionality of an instrument.

13. The sample plate according to claim 1, wherein the fluorescent mineral or the substance that includes a fluorescent mineral is used as a fluorescence standard in order to calibrate or read out a chemical reaction or a biochemical or diagnostic assay or test.

14. The sample plate according to claim 13, wherein the assay or test to be read is a glucose monitoring test, immunoassay, protein detection assay, cell assay, cell count test, hormone test, water analysis, food analysis, surface analysis, or nucleic acid test or nucleic acid amplification test.

15. The sample plate according to claim 1, wherein the fluorescent mineral or the substance that includes a fluorescent mineral is used as a fluorescence standard in that it is applied as a marker to a molecule.

16. The sample plate according to claim 1, wherein the fluorescent mineral or the substance that includes a fluorescent mineral is used as a fluorescence standard to identify a product or an object.

17. The sample plate according to claim 1, wherein the fluorescent mineral or the substance that includes a fluorescent mineral is used as a fluorescence standard to measure and, if applicable, to control temperature.

18. The sample plate according to claim 1, wherein the sample plate is comprised entirely of the fluorescent mineral, and/or the substance that includes a fluorescent mineral.

19. The sample plate according to claim 1, wherein the fluorescent mineral, and/or the substance that includes a fluorescent mineral, is embedded in a carrier matrix.

20. The sample plate according to claim 1, wherein the sample plate is a microtiter plate with a plurality of wells.

21. The sample plate according to claim 1, wherein the fluorescent mineral and/or the substance that includes a fluorescent mineral, for use as a fluorescence standard, is located in at least one of the wells of the sample plate, such that said substance is removable and/or is permanently bonded to the sample plate.

22. The sample plate according to claim 1, wherein the fluorescent mineral comprises a plurality of small particles, wherein said particles are embedded it a polymer.

23. The sample plate according to claim 1, wherein the sample plate is a capillary tube a cell, a reaction vessel, a gel, a polymer, a tube, and/or a microfluidic chip.

24. A detector for electromagnetic radiation comprising the sample plate according to claim 1.

* * * * *